(12) United States Patent
Bruszewski

(10) Patent No.: US 8,419,782 B2
(45) Date of Patent: Apr. 16, 2013

(54) PRECISE POSITIONING PROSTHESIS DELIVERY SYSTEM AND METHOD

(75) Inventor: Walter Bruszewski, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 327 days.

(21) Appl. No.: 12/420,951

(22) Filed: Apr. 9, 2009

(65) Prior Publication Data

US 2010/0262217 A1 Oct. 14, 2010

(51) Int. Cl.
*A61F 2/06* (2006.01)

(52) U.S. Cl.
USPC ......... 623/1.11; 606/198; 606/194; 623/1.12; 623/1.13; 623/1.23

(58) Field of Classification Search .................. 623/1.12, 623/1.23, 1.34, 1.35, 1.36; 606/194, 198
See application file for complete search history.

(56) References Cited

U.S. PATENT DOCUMENTS

| 5,617,878 | A | | 4/1997 | Taheri | |
|---|---|---|---|---|---|
| 5,755,777 | A | * | 5/1998 | Chuter | 623/1.11 |
| 6,451,053 | B1 | * | 9/2002 | Dehdashtian et al. | 623/1.34 |
| 6,524,335 | B1 | * | 2/2003 | Hartley et al. | 623/1.13 |
| 6,827,726 | B2 | * | 12/2004 | Parodi | 606/194 |
| 7,122,052 | B2 | * | 10/2006 | Greenhalgh | 623/1.35 |
| 7,264,632 | B2 | | 9/2007 | Wright et al. | |
| 2003/0176912 | A1 | * | 9/2003 | Chuter et al. | 623/1.13 |
| 2003/0199967 | A1 | * | 10/2003 | Hartley et al. | 623/1.13 |
| 2004/0230287 | A1 | * | 11/2004 | Hartley et al. | 623/1.12 |
| 2005/0033400 | A1 | * | 2/2005 | Chuter | 623/1.11 |
| 2005/0288765 | A1 | * | 12/2005 | Taheri | 623/1.12 |
| 2007/0208256 | A1 | | 9/2007 | Marilla | |
| 2007/0225797 | A1 | * | 9/2007 | Krivoruhko | 623/1.35 |
| 2007/0233220 | A1 | * | 10/2007 | Greenan | 623/1.11 |
| 2008/0071343 | A1 | * | 3/2008 | Mayberry et al. | 623/1.11 |
| 2008/0167704 | A1 | * | 7/2008 | Wright et al. | 623/1.12 |

* cited by examiner

*Primary Examiner* — Gary Jackson
*Assistant Examiner* — Katrina Stransky

(57) ABSTRACT

A method of prosthesis delivery comprises advancing first, second and third guidewires through a first vessel, positioning the second guidewire in a second vessel that branches from the first vessel, positioning the third guidewire in a third vessel that branches from the first vessel, advancing a prosthesis over the first, second, and third guidewires to the vicinity of one of the second and third vessels, and deploying the prosthesis. The prosthesis can comprise a tubular stent-graft having a first eyelet adapted to receive a guidewire and a second eyelet adapted to receive a guidewire. A prosthesis delivery system comprises prosthesis delivery apparatus comprising a sheath, a prosthesis having a plurality of eyelets and being disposed in the sheath, a first guidewire tube for receiving a first guidewire and being positioned inside the prosthesis; a second guidewire tube for receiving a second guidewire and being positioned inside the prosthesis, and a third guidewire tube for receiving a third guidewire and being positioned inside the prosthesis.

18 Claims, 12 Drawing Sheets

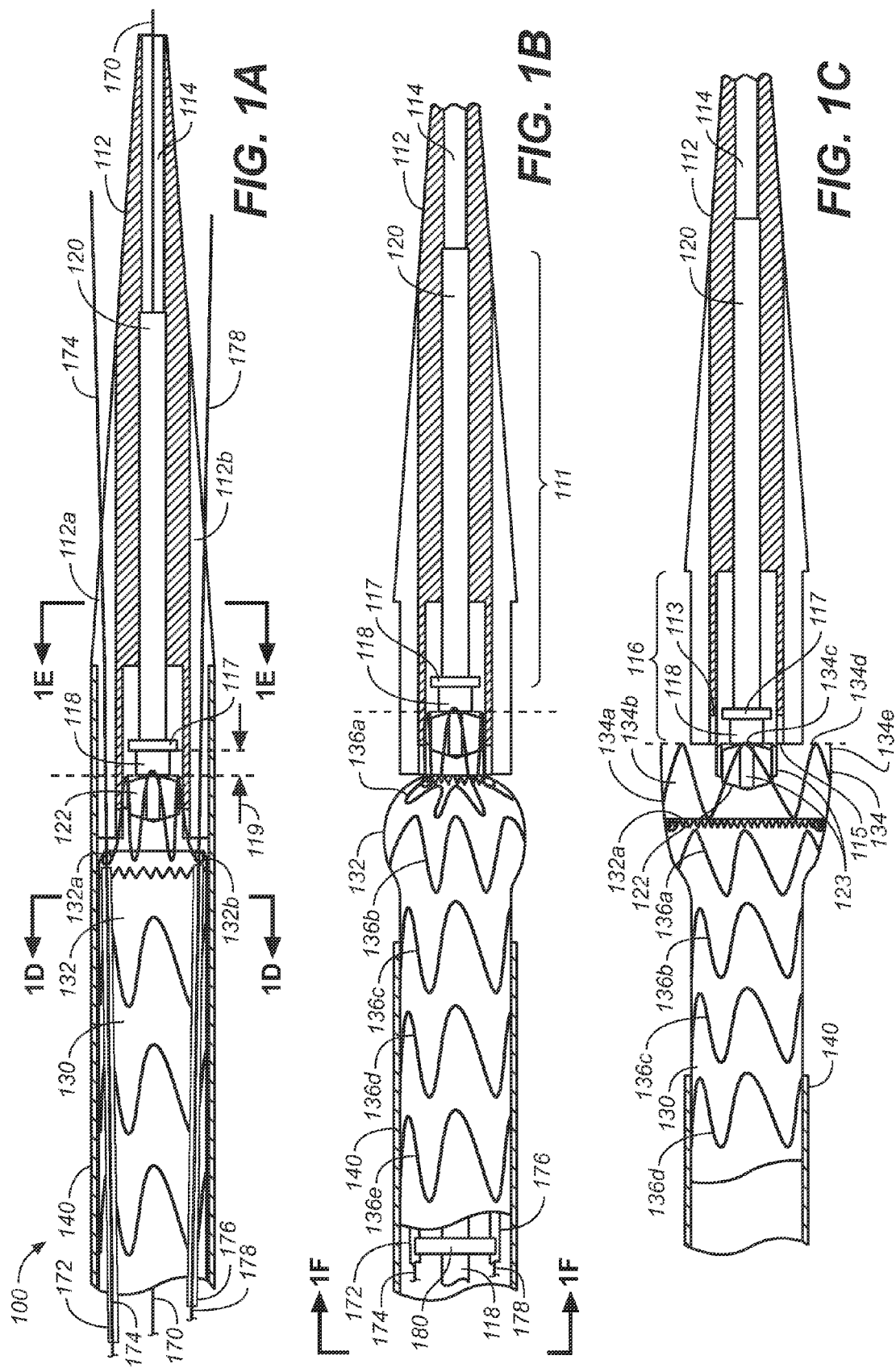

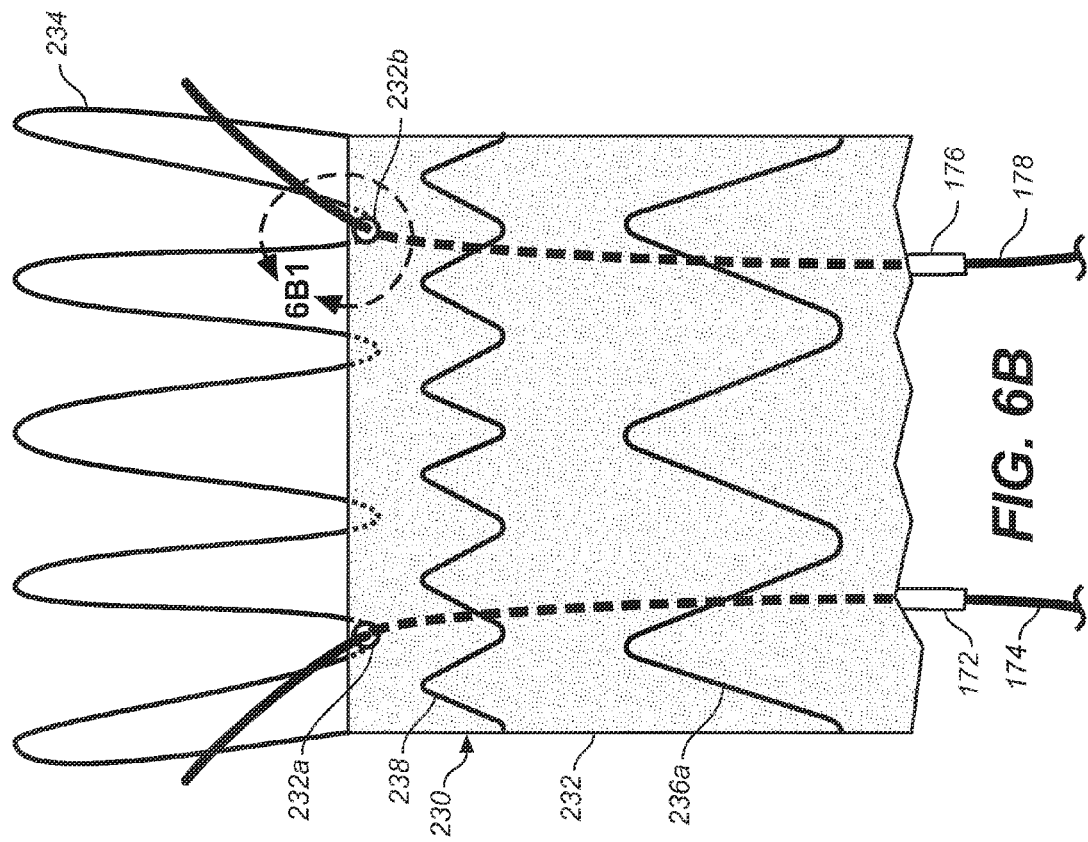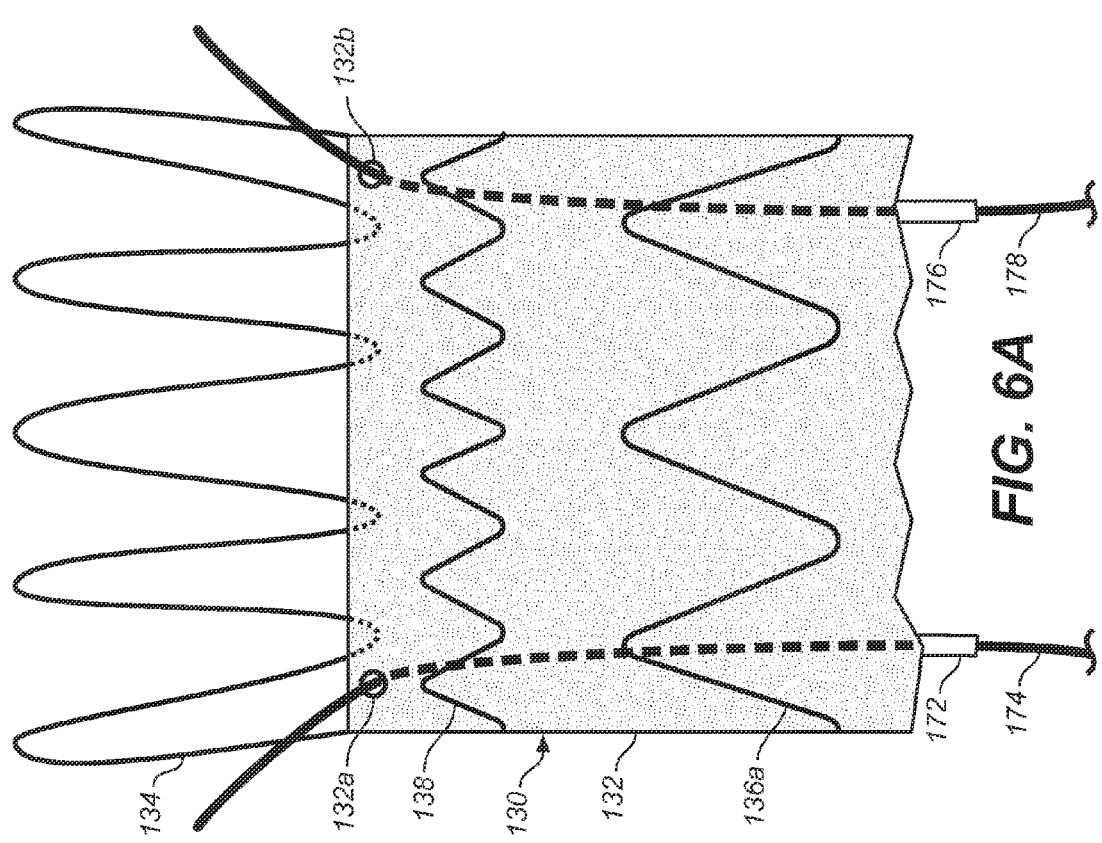

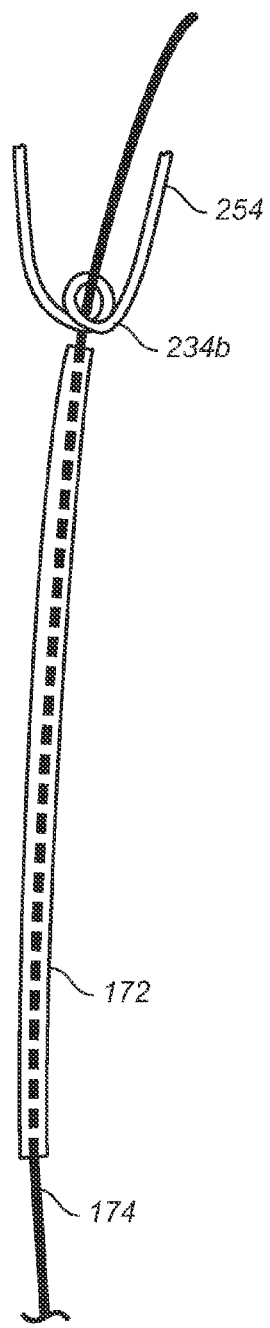
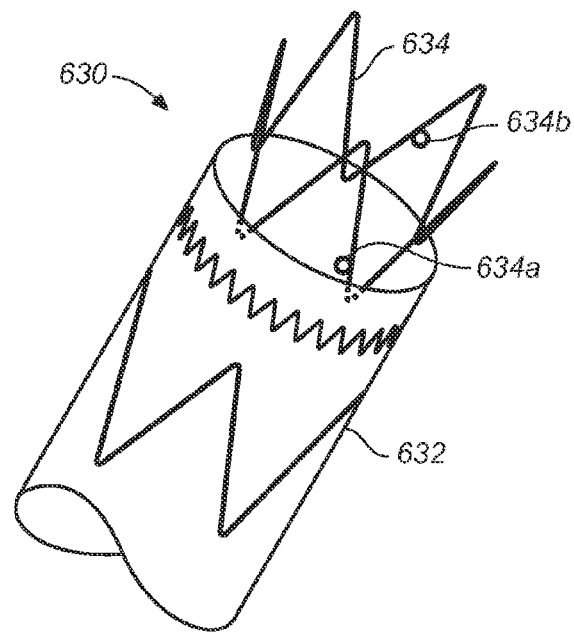
*FIG. 6B1*    *FIG. 6G*

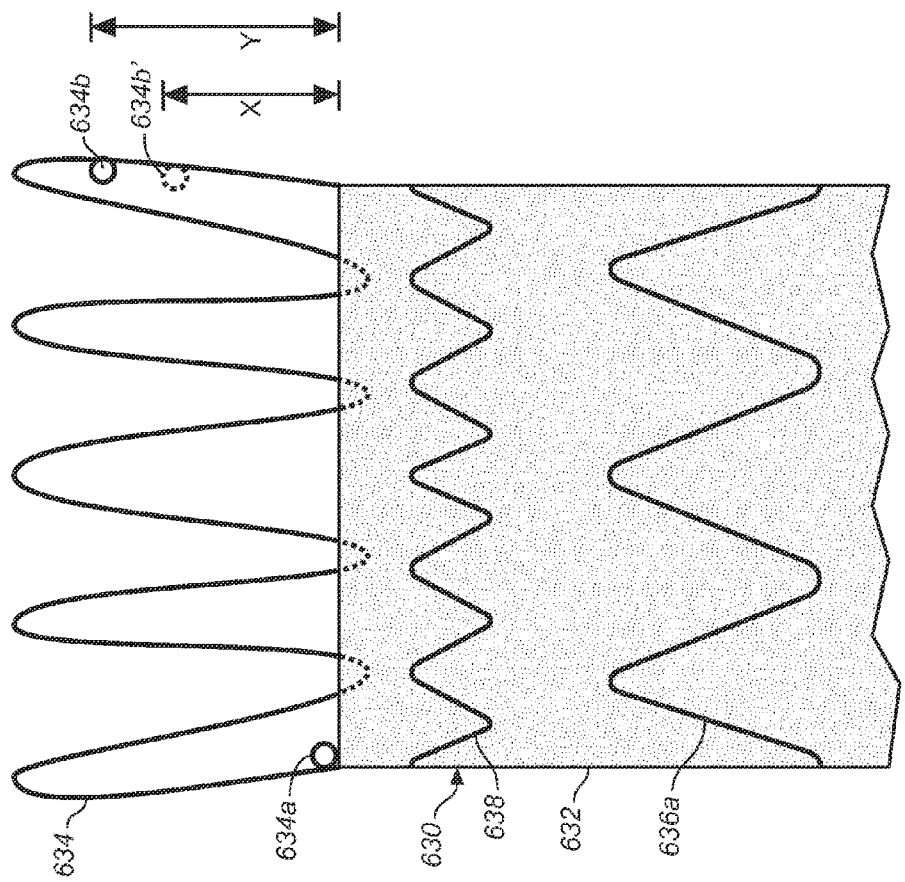
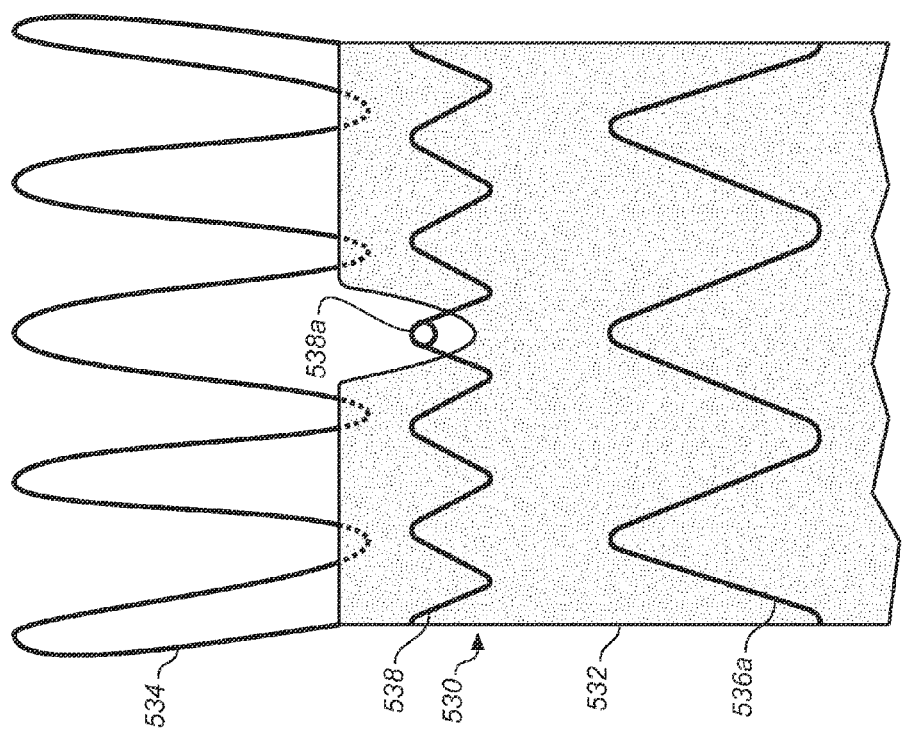

PRECISE POSITIONING PROSTHESIS DELIVERY SYSTEM AND METHOD

FIELD OF THE INVENTION

The invention relates to grafts suitable for placement in a human body lumen such as an artery.

BACKGROUND OF THE INVENTION

Tubular prostheses such as stents, grafts, and stent-grafts (e.g., stents having an inner and/or outer covering comprising graft material and which may be referred to as covered stents) have been used to treat abnormalities in passageways in the human body. In vascular applications, these devices often are used to replace or bypass occluded, diseased or damaged blood vessels such as stenotic or aneurysmal vessels. For example, it is well known to use stent-grafts, which comprise biocompatible graft material (e.g., polyester material such as Dacron® fabric, polytetrafluoroethylene PTFE, or expanded polytetrafluoroethylene (ePTFE) or some other polymer) supported by a framework (e.g., one or more stent or stent-like structures) to treat or isolate aneurysms. The framework provides mechanical support and the graft material or liner provides a blood barrier. Approaches for making stent-grafts have included sewing one or more stents or annular metallic spring elements, which may have a sinusoidal configuration, to woven materials, ePTFE, PTFE or Dacron® fabric. Other approaches have included electrospinning the stent structure with a polymer or dip coating. Many stent-grafts have a bare-spring or crown stent attached to one or both of its ends to enhance fixation between the stent-graft and the vessel where it is deployed. The bare-spring or crown stent can be referred to as an anchoring device.

In treating an aneurysm, the graft material typically forms a blood impervious lumen to facilitate endovascular exclusion of the aneurysm. When using a stent-graft, the stent-graft typically is placed so that one end of the stent-graft is situated proximal to or upstream of the diseased portion of the vessel and the other end of the stent-graft is situated distal to or downstream of the diseased portion of the vessel. In this manner, the stent-graft extends through and spans the aneurysmal sac and extends beyond the proximal and distal ends thereof to replace or bypass the dilated wall. The graft material typically forms a blood impervious lumen to facilitate endovascular exclusion of the aneurysm.

Such prostheses can be implanted in an open surgical procedure or with a minimally invasive endovascular approach. Minimally invasive endovascular stent-graft use is preferred by many physicians over traditional open surgery techniques where the diseased vessel is surgically opened, and a graft is sutured into position bypassing the aneurysm. The endovascular approach, which has been used to deliver stents, grafts, and stent-grafts, generally involves cutting through the skin to access a lumen of the vasculature. Alternatively, vascular access may be achieved percutaneously via successive dilation at a less traumatic entry point. Once access is achieved, the stent-graft can be routed through the vasculature to the target site. For example, a stent-graft delivery catheter loaded with a stent-graft can be percutaneously introduced into the vasculature (e.g., into a femoral artery) and the stent-graft delivered endovascularly across the aneurysm where it is deployed.

When using a balloon expandable stent-graft, balloon catheters generally are used to expand the stent-graft after it is positioned at the target site. When, however, a self-expanding stent-graft is used, the stent-graft generally is radially compressed or folded and placed at the distal end of a sheath or delivery catheter and self expands upon retraction or removal of the sheath at the target site. More specifically, a delivery catheter having coaxial inner and outer tubes arranged for relative axial movement therebetween can be used and loaded with a compressed self-expanding stent-graft. The stent-graft is positioned within the distal end of the outer tube (sheath) and in front of a stop fixed to the distal end of the inner tube.

Regarding proximal and distal positions referenced herein, the proximal end of a prosthesis (e.g., stent-graft) is the end closest to the heart (by way of blood flow path) whereas the distal end is the end furthest away from the heart during deployment. In contrast, the distal end of a catheter is usually identified as the end that is farthest from the operator, while the proximal end of the catheter is the end nearest the operator (handle).

Once the catheter is positioned for deployment of the stent-graft at the target site, the inner tube is held stationary and the outer tube (sheath) withdrawn so that the stent-graft is gradually exposed and expands. An exemplary stent-graft delivery system is described in U.S. Pat. No. 7,264,632 to Wright et al., the disclosure of which is hereby incorporated herein in its entirety by reference thereto.

Although the endovascular approach is much less invasive, and usually requires less recovery time and involves less risk of complication as compared to open surgery, there can be concerns with alignment of prostheses in relatively complex applications such as one involving branch vessels. The procedure becomes more complicated when more than one branch vessel is treated. For example, when treating an aortic abdominal aneurysm, if a non-fenestrated stent-graft is placed above the distal edge of the renal ostia, it can compromise blood flow.

In another example where additional challenges are presented, an aortic abdominal aneurysm is to be treated and its proximal neck is diseased or damaged to the extent that it cannot support an effective seal and connection with a prosthesis. In this case, grafts or stent-grafts have been provided with fenestrations or openings formed in their side wall below a proximal portion thereof. The fenestrations or openings are positioned to be aligned with the renal arteries and the proximal portion is secured to the aortic wall above the renal arteries. To ensure alignment of the prostheses fenestrations and branch vessels, current techniques involve placing guidewires through each fenestration and branch vessel (e.g., artery) prior to releasing the main device or prosthesis. An angiographic catheter may be used to provide detection of the branch vessels and preliminary prosthesis positioning.

U.S. Pat. No. 5,617,878 to Taheri discloses a method comprising interposition of a graft at or around the intersection of major arteries and thereafter, use of intravenous ultrasound or angiogram to visualize and measure the point on the graft where the arterial intersection occurs. A laser or cautery device is then interposed within the graft and used to create an opening in the graft wall at the point of the intersection. A stent is then interposed within the graft and through the created opening of the intersecting artery.

U.S. patent application Ser. No. 11/276,512 to Marilla, entitled Multiple Branch Tubular Prosthesis and Methods, filed Mar. 3, 2006, and co-owned by the assignee of the present application, discloses positioning in an endovascular prosthesis an imaging catheter (intravenous ultrasound device (IVUS)) having a device to form an opening in the side wall of the prosthesis. The imaging catheter detects an area of the prosthesis that is adjacent to a branch passageway (e.g., a renal artery), which branches from the main passageway in which the prosthesis has been deployed. The imaging catheter opening forming device is manipulated or advanced to form an opening in that area of the prosthesis to provide access to the branch passageway. The imaging catheter also can include a guidewire that can be advanced through the opening.

In sum, alignment of a stent-graft with the distal edge of the renal ostia is challenging and there remains a need to develop and/or improve prosthesis deployment apparatus and methods for endoluminal or endovascular applications.

SUMMARY OF THE INVENTION

The present invention involves improvements in using a prosthesis delivery to precisely position an endoluminal prosthesis. In one embodiment according to the invention, a method of prosthesis delivery comprises advancing first, second and third guidewires through a first vessel; positioning the second guidewire in a second vessel that branches from the first vessel; positioning the third guidewire in a third vessel that branches from the first vessel; advancing a prosthesis over the first, second, and third guidewires to the vicinity of one of the second and third vessels; and deploying the prosthesis.

In another embodiment according to the invention, prosthesis comprises a tubular stent-graft comprising a tubular graft and a plurality of annular spring elements secured to the tubular graft; one of the annular spring elements having a first eyelet adapted to receive a first branch guidewire; and one of the annular spring elements and the tubular graft having a second eyelet adapted to receive a second branch guidewire.

In another embodiment according to the invention, a prosthesis delivery system comprises prosthesis delivery apparatus comprising a sheath; a prosthesis having a plurality of eyelets and being disposed in the sheath; a first guidewire tube for receiving a first guidewire and being positioned inside the prosthesis; a second guidewire tube for receiving a second guidewire and being positioned inside the prosthesis; and a third guidewire tube for receiving a third guidewire and being positioned inside the prosthesis.

BRIEF DESCRIPTION OF THE DRAWINGS

FIG. 1A is an enlarged view of the distal end of the system shown in FIG. 1 encircled by line 1A.

FIG. 1B illustrates partial deployment of the stent-graft illustrated in FIG. 1A.

FIG. 1C illustrates full deployment of one end of the stent-graft of FIG. 1A.

FIG. 2 illustrates endovascularly advancing stent-graft delivery apparatus components of the system of FIG. 1 over three guidewires that have been previously placed beyond an aortic aneurysm with the distal ends of two of the guidewires in branch arteries, which in this illustration correspond to the renal arteries, FIG. 3 illustrates advancing the apparatus of FIG. 1 to the branch arteries, FIG. 4 illustrates partial deployment of the apparatus stent-graft where the stent-graft retaining sheath is partially retracted and then the stent-graft tip capture mechanism is advanced to release the stent-graft proximal spring, and FIG. 5 shows the stent-graft fully deployed after the stent-graft restraining sheath has been withdrawn and the remaining components of the delivery system removed.

FIG. 6A schematically illustrates one stent-graft configuration according to the invention.

FIG. 6B schematically illustrates another stent-graft configuration according to the invention.

FIG. 6B1 schematically illustrates a portion of the stent-graft shown in FIG. 6B surrounded by line 6B1 showing a crown stent loop through which one of the guidewires passes.

FIG. 6E schematically illustrates another stent-graft configuration according to the invention.

FIG. 6F schematically illustrates another stent-graft configuration according to the invention.

FIG. 6G is a perspective view of a portion of the stent-graft of FIG. 6F.

DETAILED DESCRIPTION

The following description will be made with reference to the drawings where when referring to the various figures, it should be understood that like numerals or characters indicate like elements.

In one embodiment according to the invention, prosthesis delivery apparatus is advanced over three guidewires. One of the guidewires is placed in a main vessel and each of the other two guidewires is placed in a separate branch vessel, each branching from the main vessel. With this configuration, one end of the prosthesis can be aligned with or positioned immediately distal to the distal edge of one branch vessel ostium or both branch vessel ostia. For example, one end of the prosthesis can be aligned with or immediately distal to one renal ostium or both renal ostia when placing a stent-graft in the aorta below the renal arteries. Such alignment optimizes sealing between the prostheses and the main vessel and minimizes the risk of compromising branch vessel blood flow. Other features, advantages, and embodiments according to the invention will be apparent to those skilled in the art from the following description and accompanying drawings.

Figure 1:
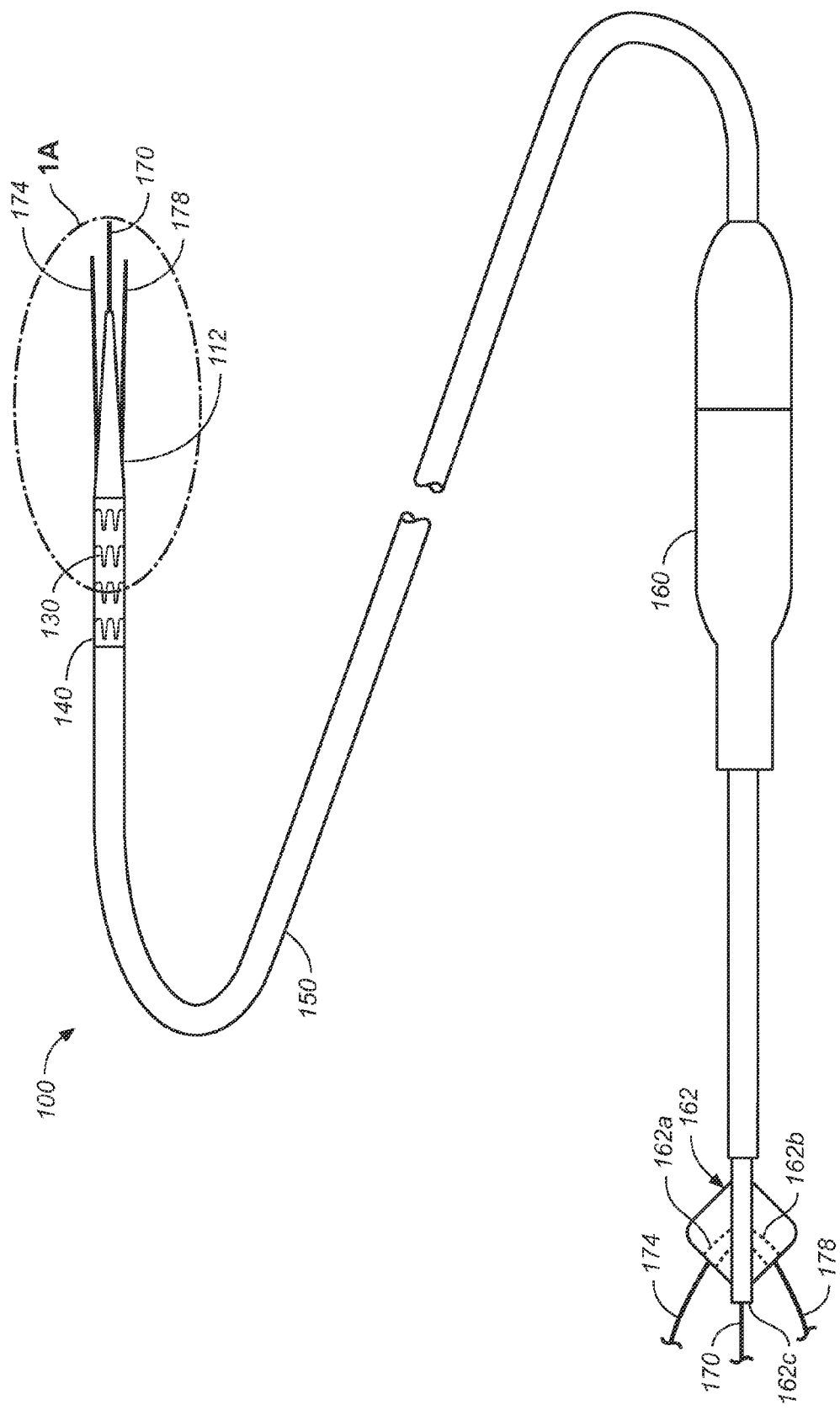
FIG. 1 illustrates one embodiment of a stent-graft delivery system according to the invention.

Referring to FIG. 1, one embodiment of a stent-graft delivery system according to the invention is shown designated with reference number 100. Stent-graft delivery system 100 includes radially compressed stent-graft 130, retractable primary sheath 140, catheter 150 in which retractable primary sheath 140 is disposed, and handle 160, which is manipulated to deploy stent-graft 130 from sheath 140. When referring to the stent-graft delivery apparatus, this will correspond to stent-graft delivery system 100 without the guidewires. Stent-graft 130 includes a plurality of annular undulating stents, which can be referred to as annular undulating spring elements, an annular undulating sealing spring, which can be referred to as and annular undulating spring element, and a crown stent, which can be referred to as a proximal spring or an annular undulating spring element. In other words, the stents, sealing spring, and crown stent can be referred to as annular spring elements. The number of annular spring elements and the number of apices in an annular spring element can vary as would be apparent to one of ordinary skill in the art.

Referring to FIG. 1A an enlarged view of the distal end of the system within circle line 1A of FIG. 1 is shown. FIGS. 1B and 1C show progressive stent-graft deployment from within retractable primary sheath 140. The vertical dashed line provides a reference line to provide correlation between FIGS. 1A-C to a common location related to the position of the end spring of the stent-graft as elements of the delivery system are manipulated to at first partially deploy and then fully deploy the proximal end of the stent-graft 130. This system could also deploy a stent alone or some other form of endoprosthesis.

A configuration of the stent-graft deployment system 100 includes a tapered tip 112 that is flexible and able to provide trackability in tight and tortuous vessels. The tapered tip 112 can include a lumen 114 allowing for passage of a guidewire for example. Other tip shapes such as bullet-shaped tips could also be used.

The retractable primary sheath 140 (preferably made of a semi-rigid material such as PTFE) in an un-retracted position contains the stent-graft 130 in a first constrained diameter configuration as shown in FIG. 1A. An outer tube 118 is located within the retractable primary sheath 140 and within the stent-graft 130 as shown in FIGS. 1A and 1C. An inner tube 120 within the outer tube 118 serves as a guidewire lumen. The inner tube 120 and the outer tube 118 can move along the longitudinal axis relative to each other and can also move along the longitudinal axis relative to the retractable primary sheath 140. A cap 115 is coupled to a distal area or end portion 111 (FIG. 1B) of the inner tube 120 and is further configured to retain at least a portion of a proximal end of the stent-graft 130 in a radially compressed configuration. Actuating members at the operator's end of the catheter create a relative force in an axial direction to provide a controlled relative axial movement between the outer tube 118 and the inner tube 120 to precisely control the release of the proximal end of the stent-graft (such as proximal springs) from the cap and from the radially compressed configuration.

FIG. 1A illustrates the system 100 with the stent-graft 130 loaded in the delivery system. The stent graft is located within the retractable primary sheath 140 in a pre-deployment un-retracted position.

FIG. 1B illustrates the system 100 with the sheath 140 partially retracted. The proximal end (tip) of the stent-graft 130 is constrained while a proximal portion of the stent-graft 130 (that is now exposed due to the partial retraction of the sheath 140) between the end of the sheath 140 and the constrained proximal end (tip) is partially deployed, which allows longitudinal repositioning of the stent graft before releasing the proximal end (the release of the proximal end of the stent graft prevents repositioning of the stent graft in a direction toward the proximal end of the stent graft, while depending on the degree of expansion and contact between the stent graft and the wall of the vessel in which the stent graft is being deployed, some pull down (movement toward the distal end of the stent graft) of the stent graft is possible.

In FIG. 1C the proximal end of the stent-graft 130 is shown as having been deployed by the controlled relative axial movement between the inner tube 120 and the outer tube 118. In particular, as shown in FIGS. 1A-C an end cap 115 containing the proximal apices of the end spring 134 of the stent-graft can be formed from a shroud portion of the tapered tip 112 which is coupled to the distal end of the outer tube 118. Within the shroud portion (formed by tubular body portion 116 of the tapered tip 112) preferably resides a back plate 117 coupled to a distal portion or end of the outer tube 118 that serves as a proximal stop for the stent-graft 130. The tubular body portion 116 of the shroud portion may also include a support (reinforcing) ring 113 near the proximal end of the tapered tip 112 to provide additional rigidity to the cap and prevents the cap shroud portion, which is preferably made of a plastic material from stretching (or distorting) in diameter. This configuration thereby prevents premature release of the proximal end of the stent-graft constrained by the cap (premature stretching could create a gap large enough for the restrained members of the stent graft to spring loose. Additionally, a proximal lock (retainer) 122 is also coupled to a distal portion of the outer tube 118. The proximal lock 122 preferably includes at least one or a plurality of ribs (or splines) 123 that can together with the shroud portion serve as an axial constraint for the end stent-graft 130. The proximal end (or the proximal spring apices, e.g., apices 134a,b,c,d,e of the stent-graft 130 cannot deploy until the proximal end of the ribs of the proximal lock clear the end of the shroud portion of the tip.

Stent-graft 130 can include a polyester or Dacron material (forming the graft material 132' (FIG. 1A) sewn to a nitinol support structure comprising stents or spring elements 136a, b, c, d, e, f, g, h, i (see FIG. FIG. 5) using polyester sutures as is known in the art. In one example, a nitinol wire is used to form a skeletal structure that provides support, strength and stability to the stent-graft. The stent-graft can also have a support member (crown stent or spring 134) on the proximal end of the stent-graft that is left mainly uncovered by the graft material. The uncovered portion will typically have a zig zag like pattern with a predetermined number of apices protruding up. The apices form the extreme end of what is known as the proximal spring (or crown spring 134) of the stent-graft. Stent-graft 130 can be a bifurcated stent-graft as shown, for example, in FIG. 5 with bifurcated tubular graft 132.

As shown in FIG. 1A, the gap 119 between the backplate 117 and the proximal lock 122 is preferably designed to hold the protruding apices (e.g., apices 134a,b,c,d,e) of the proximal spring 134. The apices straddle the ribs 123 of the proximal lock 122 and remain trapped between the back plate and the proximal lock until the relative movement between the outer tube 118 and the inner tube 120 exposes the gap 119 and releases the apices (e.g., apices 134a,b,c,d,e) of the proximal spring as shown in FIG. 1C. In other words, the apices (e.g., apices 134a,b,c,d,e) cannot release from the ribs 123 on the proximal lock 122 while the apices remain within the shroud portion116. When the inner tube 120 and tapered tip 112 assembly are advanced forward exposing the proximal lock 122, the apices of the proximal spring release from the respective ribs 123 of the proximal lock 122. The release results in the deployment of the proximal end of the stent-graft 130 as shown in FIG. 1C. Note that while the apices of the proximal spring remain in gap 119 and within the cap or shroud portion of the tapered tip 112, the whole of the proximal spring remains axially (longitudinally) constrained as well as radially constrained. The support ring 113, usually made of metal, helps prevent the radial force of the proximal springs from distorting the shape of the tapered tip and particularly the shroud portion of the tapered tip.

Figure 1E:
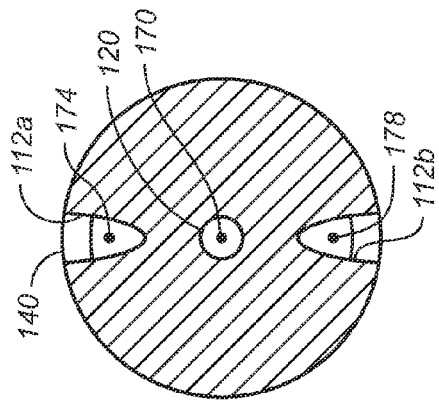
FIG. 1E is a cross-sectional view taken along line 1E-1E in FIG. 1A.
Figure 1D:
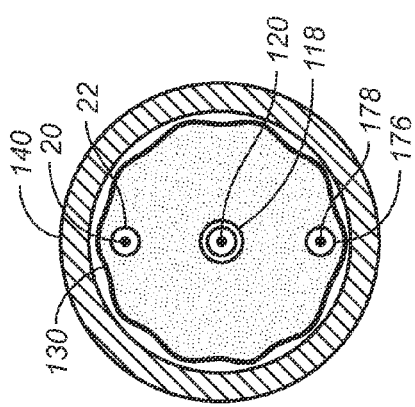
FIG. 1D is a cross-sectional view taken along line 1D-1D in FIG. 1A.
Figure 5:
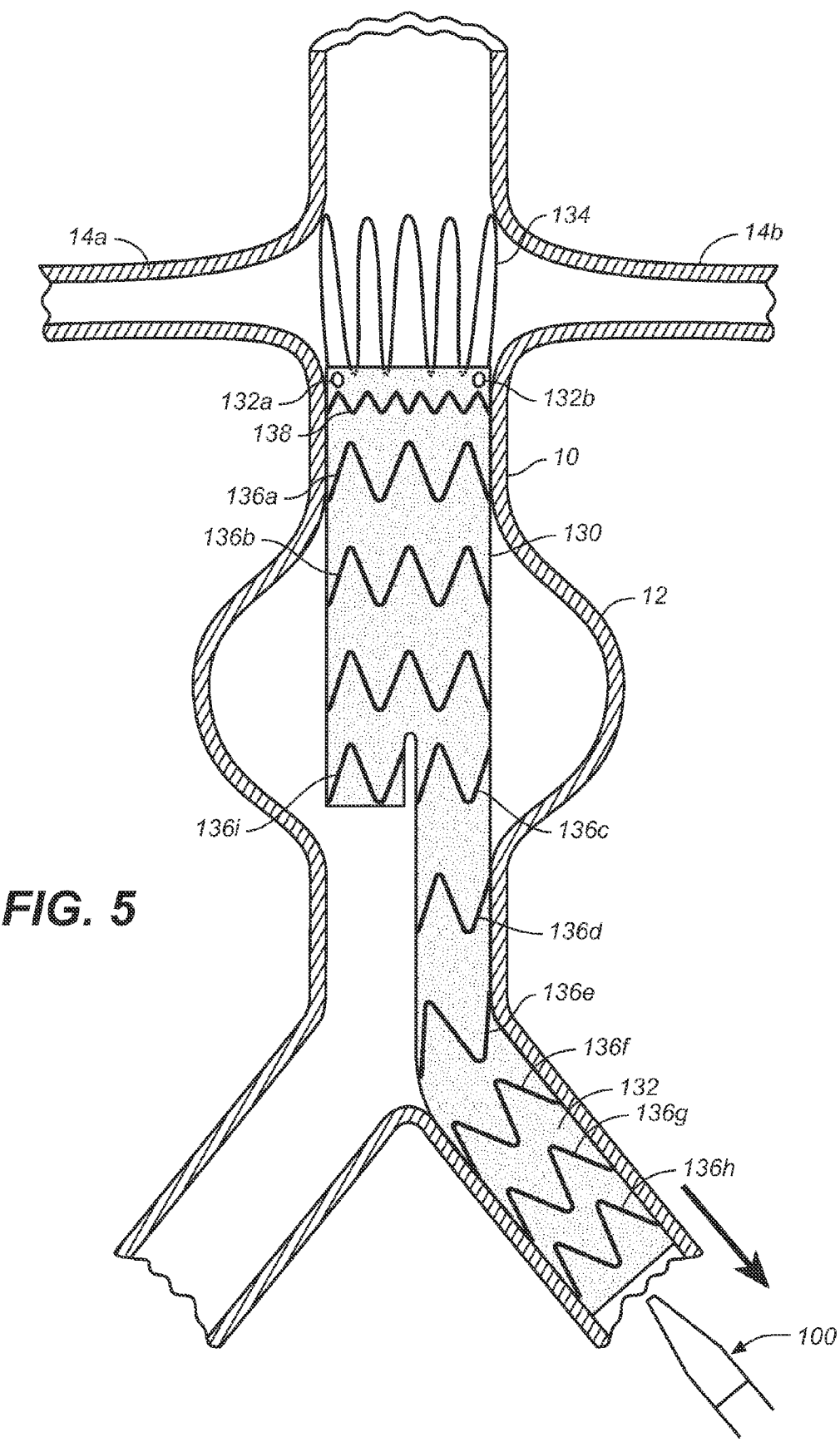

Referring to FIGS. 1A, 1D, and 1E and the bifurcated tubular graft 132 as shown in FIG. 5, the stent-graft delivery system includes separate, flexible non-concentric guidewire lumens or tubes 120, 172 and 176 all of which extend in a longitudinal direction inside stent-graft 130. First or central guidewire 170 passes through guidewire lumen or tube 120. Second guidewire 174 passes through guidewire lumen or tube 172, which has an end portion that is positioned along the inner wall surface of stent-graft 130 and in this embodiment terminates distal to the proximal edge of tubular graft 132. Guidewire 174 then exits tube or lumen 172 and passes out from stent-graft 130. In this embodiment, guidewire exits tube or lumen 172, passes through opening or eyelet 132a formed in tubular graft 132 and then through recess (channel) 112a, which is formed in tapered tip 112. Third guidewire 178 passes through guidewire lumen or tube 176, which is positioned along the inner wall surface of stent-graft 130 and in this embodiment terminates distal to the proximal edge of tubular graft 132. Guidewire 178 then exits tube or lumen 176 and passes out from stent-graft 130. In this embodiment, guidewire exits tube or lumen 176, passes through opening or eyelet 132b formed in tubular graft 132 and then through recess (channel) 112b, which is formed in tapered tip 112. Guidewires 174 and 178 are not shown in FIGS. 1B and 1C for purposes of clarity.

Recesses or channels 112a and 112b can correspond to U-shaped cut-outs formed in tapered tip 112 as shown, for example, in FIG. 1E such that guidewires 174 and 178 can exit tapered tip 112 through the exposed channels, which are circumferentially spaced (diametrically opposed) about tapered tip 112.

Figure 1G:
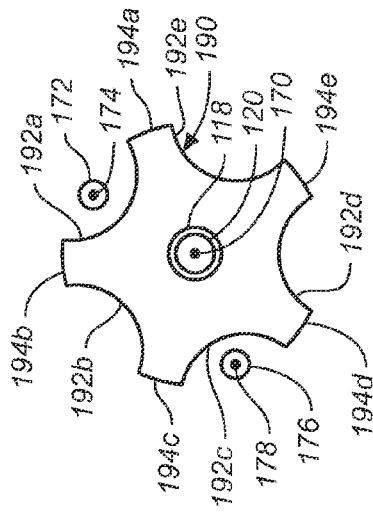
FIG. 1G depicts another configuration of a stent-graft stop according to the invention.
Figure 1F:
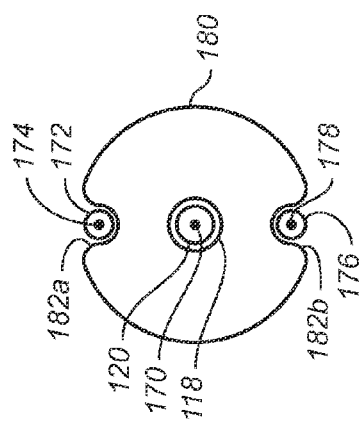
FIG. 1F depicts one configuration of a stent-graft stop according to the invention taken along line 1F-1F in FIG. 1B.

Referring to FIG. 1F, one embodiment of a stop member for stopping the stent-graft from moving backward during sheath withdrawal is shown and designated with reference numeral 180. Stop member 180 is fixedly secured to outer tube 118 and has a central opening in which outer tube 118 is fixedly positioned. Stop member 180 is generally annular or disk-shaped and includes two recesses or channels 182a and 182b through which guidewire tubes 172 and 176 extend. Guidewire tubes or lumens 120, 172, and 176 and outer tube 118 then extend back to handle assembly 160. Guidewires 170, 174, and 178 pass through handle assembly 160 and out from hub 162, which has three outlet channels 162a,b,c formed therein. Handle assembly 160 can comprise any suitable handle assembly that provides manipulation of retractable sheath 140 and tapered tip 112 such as the Xcelerant® handle assembly for the Endurant® Stent Graft manufactured by Medtronic, Inc. (Minneapolis, Minn.). Passages are provided along the length of the handle assembly to allow passage of the guidewires to hub 162.

Referring to FIG. 1G, another stop member embodiment is shown and designated with reference numeral 190. Stop member 190 has is fixedly secured to outer tube 118 and has a central opening in which outer tube 118 is fixedly positioned. Stop member 190 has a star shape with projections 192a-e and recesses or channels 194a-e formed therebetween.

One stent-graft delivery system that can be modified to include guidewire tubes 172 and 176 and for receiving guidewires 174 and 178 as described above is described in U.S. Pat. No. 7,264,632 to Wright, the disclosure of which is hereby incorporated herein in its entirety by reference thereto.

Figure 2:
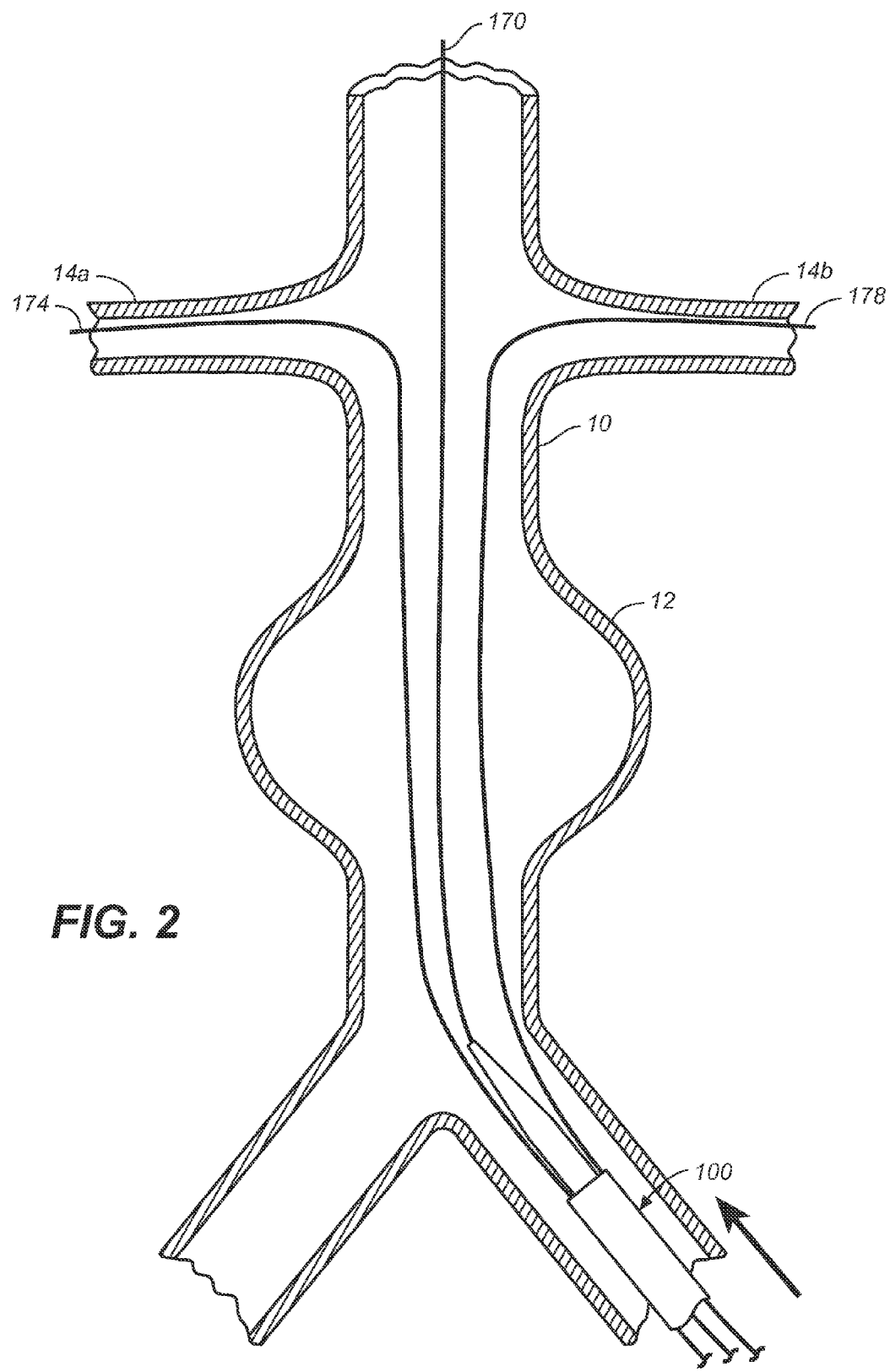
FIGS. 2-5 illustrate the steps of a method of using the system of FIG. 1 where
Figure 3:
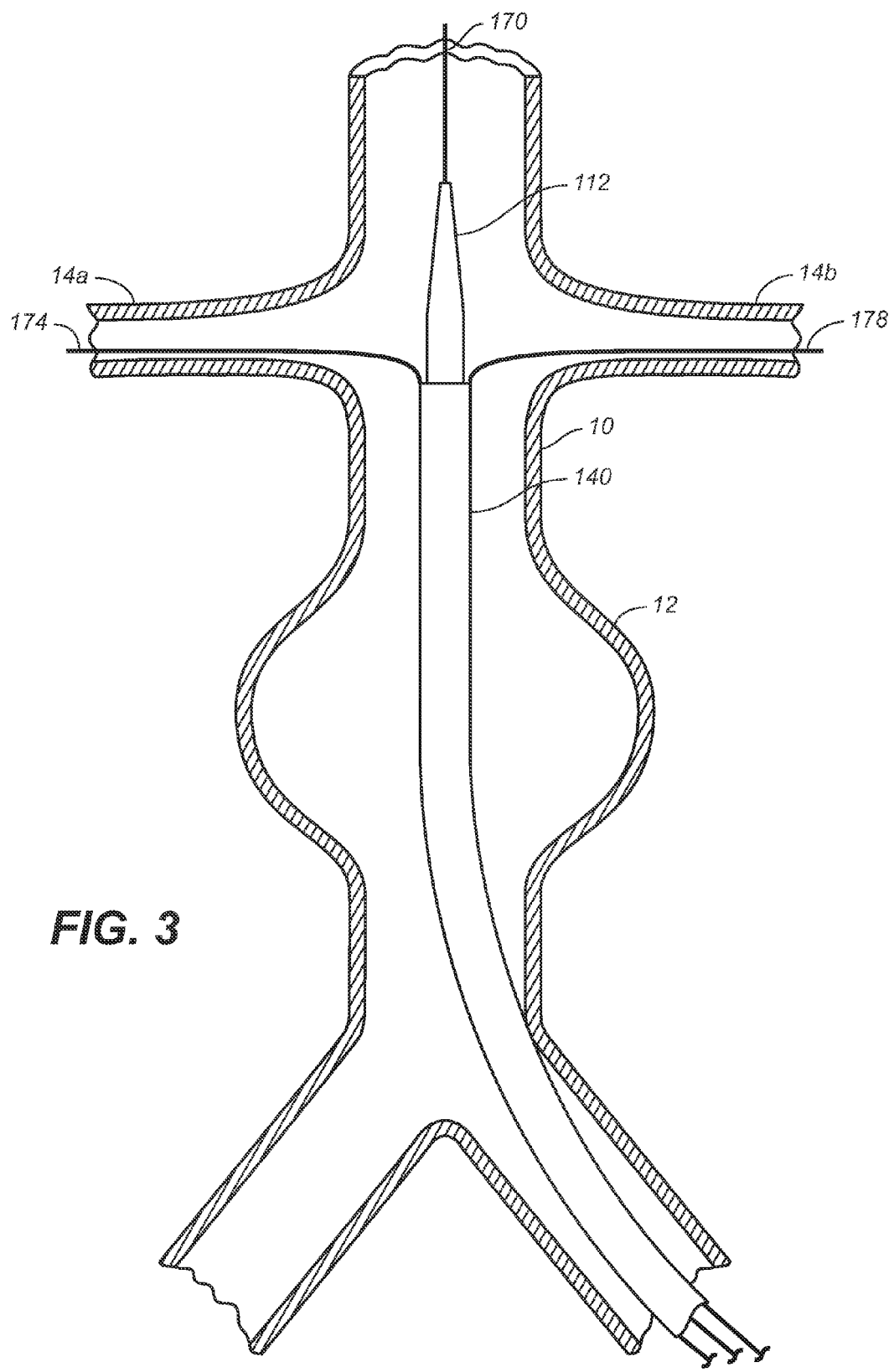
Figure 4:
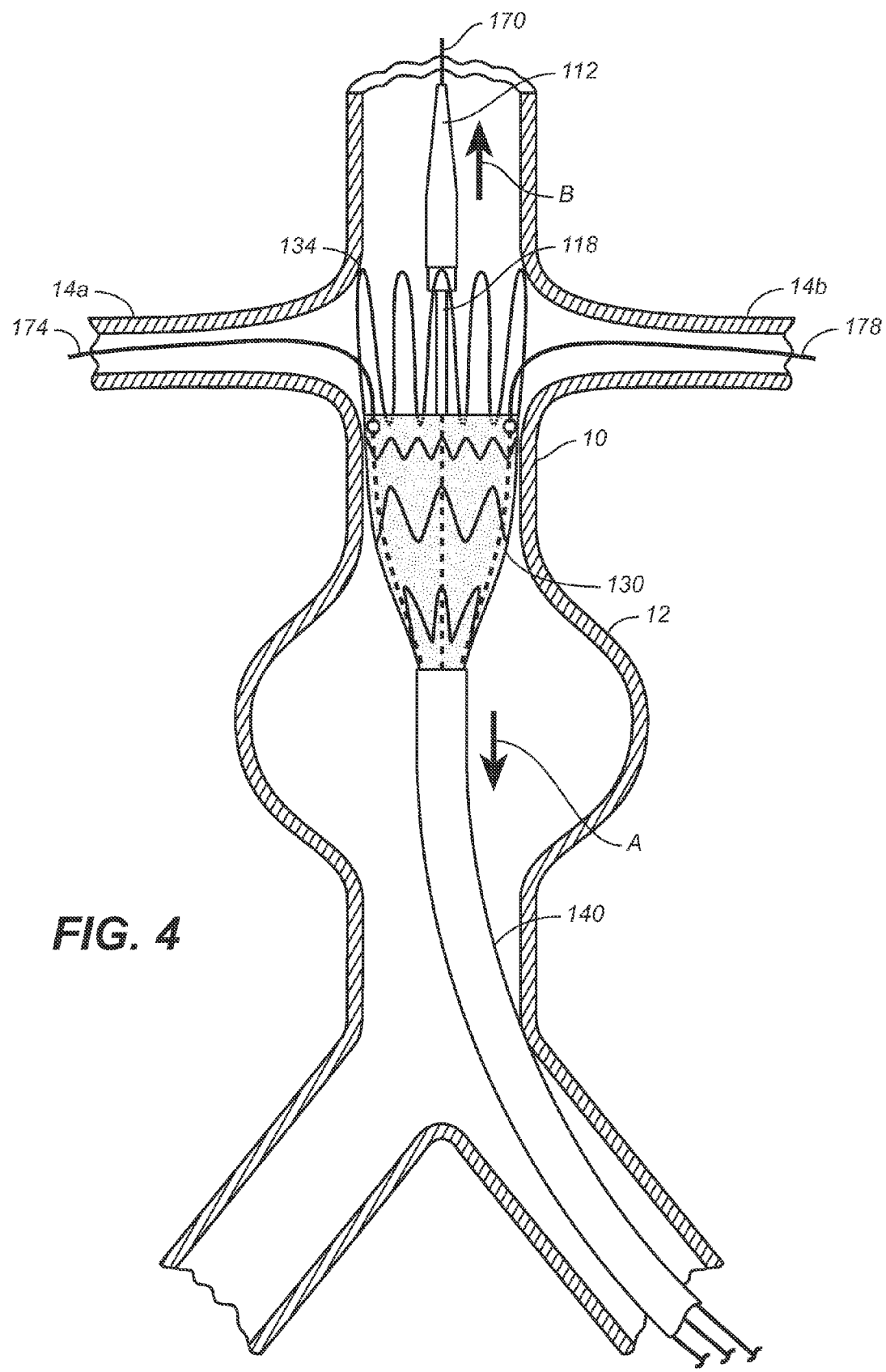

Referring to FIGS. 2-5, a method of using system 100 will be described. Guidewires 170, 174, and 178 are endovascularly positioned above an aneurysm 12 in the aorta 10 of a patient with guidewires 174 and 178 positioned in renal arteries 14a and 14b and guidewire 170 positioned above the renal arteries. The guidewires can be directed to the desired site using a known means known in the art including but not limited to a steerable guidewire catheter or a preformed catheter having a curvature suitable for advancing a respective guidewire from the aorta into a branch vessel. Then the delivery apparatus shown, for example, in FIG. 1A with the guidewires extending therethrough is advanced over guidewires 170, 174 and 178 as shown in FIG. 2. Referring to FIG. 3, the delivery apparatus is advanced so that the tubular graft 102 is positioned just below the renal arteries. The physician can advance the delivery apparatus with the stent-graft therein until guidewire 174 and/or guidewire 178 resists further advancement along guidewire 170 in the vicinity where the second and/or third guidewires enter the branch vessels. The resistance can result from the bend in either or both guidewires 174 and 178 where they exit tapered tip 112 and extend toward and into the branch vessels 14a and 14b. When the branch vessels are aligned so that the guidewire bends are aligned as shown in FIG. 3, both guidewires 174 and 178 will provide resistance. When passing through tortuous vasculature wire 174 or 178 can be tensioned and then released to assist advancing the delivery apparatus over guidewires 174 and 178.

In the next step, the physician partially retracts sheath 140 as indicated with arrow "A" (FIG. 4) (also see FIG. 1B). Subsequently, the physician advances tapered tip 112 as indicated with arrow "B" (FIG. 4) (also see FIG. 1C) to release the tip of proximal spring 134. The physician further retracts stent-graft sheath 140 until the stent-graft is fully deployed and removes the remaining components of the system as shown in FIG. 5.

FIG. 6A is an enlarged view of the stent-graft configuration shown in FIG. 1A, where stent-graft 130 includes tubular graft 132 comprising graft material having two circumferentially spaced eyelets or openings 132a,b formed therein and adjacent to the proximal edge of the tubular graft, annular undulating proximal spring 134, annular undulating stents or springs 136a-i (see also FIG. 1B), and sealing spring 138. The springs can be secured to the inner or outer wall of tubular graft 132 and secured to the graft using any conventional means such as sutures. In the illustrative embodiment, the proximal spring has it apices at one end secured to the inner wall of tubular graft 132 and the other springs and/or stents secured to the outer wall of tubular graft 132. Tubes 172 and 176 are positioned inside tubular graft 132 as described above so that guidewires 174 and 178 can pass therethrough and out from eyelets or openings 132a and 132b. Eyelets or openings 132a and 132b each can have a rim or ring to improve the openings' tear resistance. The rim or ring can comprise any suitable material such as nitinol to enhance passage of the guidewires therethrough. Further, although not shown eyelets or openings 132a and 132b can be spaced 180 degrees apart.

FIG. 6B illustrates another stent-graft configuration according to the invention. Stent-graft 230 is the same as stent-graft 130 except that tubular graft 132, proximal annular undulating spring 134, annular undulating stents or springs 136a, and sealing spring 138 are renumbered as stent-graft 230, tubular member 232, proximal annular undulating spring 234, annular undulating stents or springs 236a, and sealing spring 238, and annular undulating spring 234 includes two eyelets or loops formed therein at the base of two apices or the base of two troughs of the undulating element. The eyelets formed in undulating spring 234 are aligned with eyelets or openings 232a,b formed in tubular graft 232 and hidden from view in FIG. 6B. However, one eyelet or loop is shown in FIG. 6B1 and numbered 234a. The second of the two eyelets has the same construction and configuration. Both of the eyelets (or loops) can be stitched to tubular graft 232 around eyelets or openings 232a,b. Further, although not shown the undulating spring eyelets or loops can be spaced 180 degrees apart.

Figure 6D:
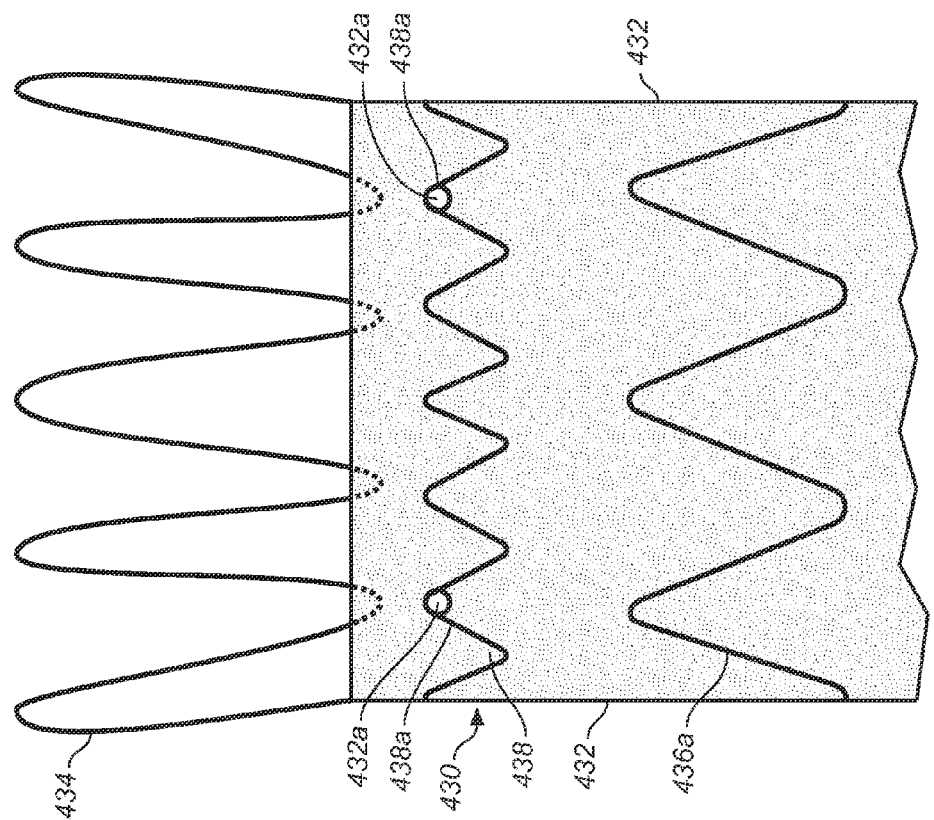
FIG. 6D schematically illustrates another stent-graft configuration according to the invention.
Figure 6C:
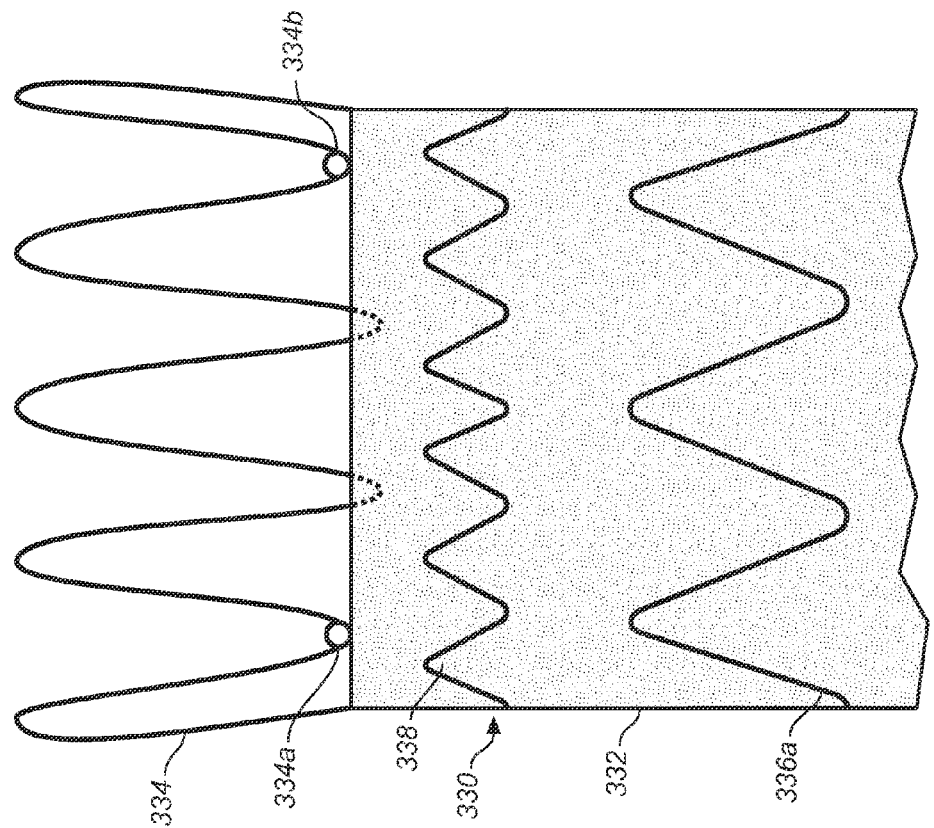
FIG. 6C schematically illustrates another stent-graft configuration according to the invention.

FIG. 6C illustrates another stent-graft configuration according to the invention. Stent-graft 330 is the same as stent-graft 130 except that tubular graft 132, proximal annular undulating spring 134, annular undulating stents or springs 136a, and sealing spring 138 are renumbered as stent-graft 330, tubular member 332, proximal annular undulating spring 334, annular undulating stents or springs 336a, and sealing spring 338, and annular undulating spring 334 includes two eyelets or loops 334a,b formed therein at the base of two apices or the base of two troughs of the undulating element where eyelets or loops 334a,b do not overlap tubular graft 332. As shown in the FIG. 6C, the troughs where eyelets or loops 334a,b are formed, do not extend axially as far as the other troughs of undulating spring 134 and do not extend of tubular graft 332. Eyelets or loops 334a,b have the same construction and configuration as eyelet or loop 234b shown in FIG. 6B1. Further, although not shown the undulating spring eyelets or loops 334a and 334b can be spaced 180 degrees apart.

FIG. 6D illustrates another stent-graft configuration according to the invention. Stent-graft 430 is the same as stent-graft 130 except that tubular graft 132, proximal annular undulating spring 134, annular undulating stents or springs 136a-e, and sealing spring 138 are renumbered as stent-graft 430, tubular member 432, proximal annular undulating spring 434, annular undulating stents or springs 436a, and sealing spring 438, and annular undulating sealing spring 438 includes two eyelets or loops 438a,b formed therein at the upper region of two apices or the peak of two undulations in the undulating element. Eyelets or loops 434a,b, which can be stitched to tubular graft 432, have the same construction and configuration as eyelet or loop 234b shown in FIG. 6B1 and surround openings in tubular graft 432 through which the guidewires can extend. Further, although not shown the undulating spring eyelets or loops 434a and 434b can be spaced 180 degrees apart.

FIG. 6E illustrates another stent-graft configuration according to the invention. Stent-graft 530 is the same as stent-graft 430 except that tubular graft 332, proximal annular undulating spring 334, annular undulating stents or springs 336a, and sealing spring 338 are renumbered as stent-graft 530, tubular member 532, proximal annular undulating spring 534, annular undulating stents or springs 536a, and sealing spring 538, and tubular graft has diametrically opposed cut outs aligned with the sealing spring eyelets or loops. Eyelet or loop 538a is shown with the other eyelet or loop being hidden from view. The sealing spring eyelets or loops (see, e.g., eyelet or loop 538a) have the same construction and configuration as eyelet or loop 234b shown in FIG. 6B1. Further, although not shown the undulating spring eyelets or loops 534a and 534b can be spaced other than 180 degrees apart.

Figure 7:
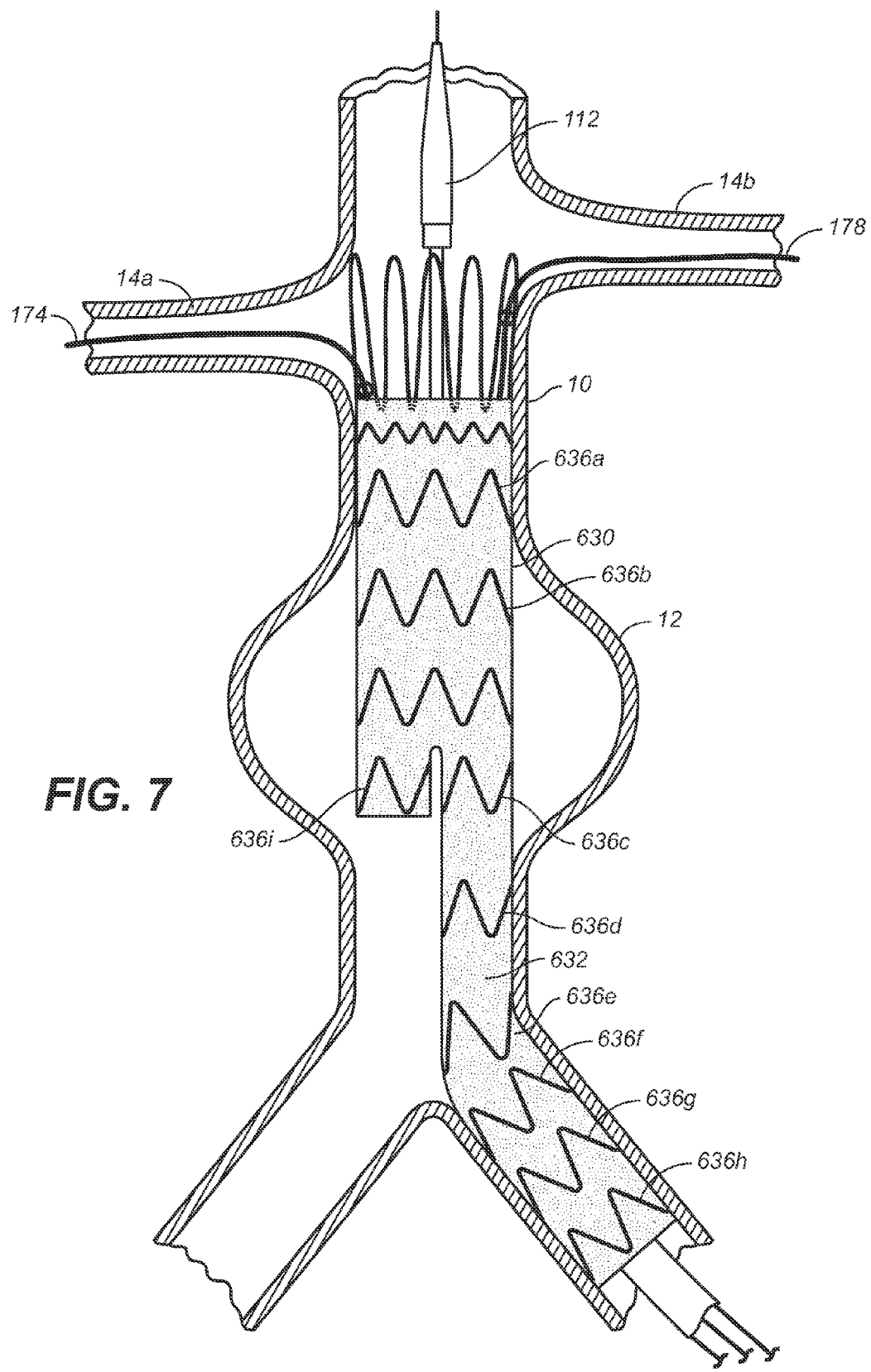
FIG. 7 schematically illustrates the stent graft of FIG. 6G aligned with branch vessels and deployed.

FIG. 6F illustrates another stent-graft configuration according to the invention. Stent-graft 630 is the same as stent-graft 130 except that tubular graft 132, proximal annular undulating spring 134, annular undulating stents or springs 136a-i, and sealing spring 138 are renumbered as stent-graft 630, tubular member 632, proximal annular undulating spring 634, annular undulating stents or springs 636a-i, and sealing spring 638, and annular undulating spring 634 includes two eyelets or loops 634a,b formed therein. Eyelets or loops 634a,b do not overlap tubular graft 632 and are spaced different distances from the distal edge of tubular graft 632 to accommodate laterally spaced branch arteries as shown, for example, in FIG. 7. In the illustrative embodiment, eyelet or loop 634a is adjacent to the proximal edge of tubular graft 632 and eyelet or loop 634b is positioned away from the proximal edge of the graft two-thirds the length of the non-overlapping portion an undulation in proximal spring 634 as generally indicated with reference character "Y." In another variation, eyelet or loop 634b is replaced with eyelet or loop 634b', which is positioned away from the proximal edge of the graft one-half the length of the non-overlapping portion an undulation in proximal spring 634 as generally indicated with reference character "X." Eyelets or loops 634a,b and 634b' have the same construction and configuration as eyelet or loop 234b shown in FIG. 6B1. Undulating spring eyelets or loops 634a and 634b or eyelets or loops 534a and 634b can be spaced 180 degrees apart or circumferentially spaced about undulating spring 634 a different degree. FIG. 7 illustrates alignment and deployment of stent-graft 630 using eyelets or loops 634a,b and guidewires 174 and 178.

Any feature described in any one embodiment described herein can be combined with any other feature or features of any of the other embodiments or features described herein. Furthermore, variations and modifications of the devices and methods disclosed herein will be readily apparent to persons skilled in the art.

What is claimed is:

1. A method of prosthesis delivery comprising:
   advancing first, second and third guidewires through a first vessel;
   positioning the second guidewire in a second vessel that branches from the first vessel;
   positioning the third guidewire in a third vessel that branches from the first vessel;
   advancing a prosthesis delivery apparatus having a sheath and a tapered distal tip over the first, second, and third guidewires to the vicinity of one of said second and third vessels, wherein during advancement of the prosthesis delivery apparatus thereover each of the first, second and third guidewires extends through a respective channel or lumen formed in the tapered distal tip and through a prosthesis held within the sheath of the prosthesis delivery apparatus and wherein the prosthesis delivery apparatus and the prosthesis are advanced together until at least one of the second and third guidewires resists further advancement thereof in the vicinity where the at least one of the second and third guidewires enters its respective second or third vessel due to a bend in the at least one of the second and third guidewires where it exits the tapered distal tip; and
   deploying the prosthesis in the main vessel, wherein the prosthesis includes a tubular graft of a graft material and wherein the prosthesis is deployed such that a proximal edge of the tubular graft is positioned within the main vessel to align with or to be positioned immediately distal of a distal edge of at least one of the ostia of the second and third vessels.

2. The method of claim 1 wherein the prosthesis is a stent-graft having at least one spring element secured to the graft material of the tubular graft.

3. The method of claim 2 wherein the prosthesis delivery apparatus and the stent-graft are advanced until the second guidewire resists further advancement thereof in the vicinity where the second guidewire enters the second vessel due to a bend in the second guidewire where it exits the tapered distal tip.

4. The method of claim 2, wherein the prosthesis delivery apparatus and the stent-graft are advanced until the second and third guidewires resist further advancement thereof in the vicinity where the second guidewire enters the second vessel and the third guidewire enters the third vessel due to respective bends in the second and third guidewires where they exit the tapered distal tip.

5. A prosthesis delivery system comprising:
   a delivery apparatus comprising a sheath and a tapered distal tip;
   a stent-graft being disposed in said sheath, said stent-graft including a tubular graft having a first end and a second end and comprising graft material having an eyelet formed therein at said first end that is sized to receive only a guidewire therethrough, said stent-graft including at least one undulating spring element having a distal end secured to said graft material adjacent to the eyelet with a remainder of the spring element extending away from an edge of said first end of said tubular graft;

a first guidewire tube having a first guidewire disposed therethrough, the first guidewire tube being positioned inside said stent-graft such that a distal opening of the first guidewire tube aligns with the eyelet such that the first guidewire extends from the distal opening of the first guidewire tube and through the eyelet;

a second guidewire tube having a second guidewire disposed therethrough, the second guidewire tube being positioned inside said stent-graft; and a third guidewire tube having a third guidewire disposed therethrough and being positioned inside said stent-graft, wherein each of said first, second and third guidewires extends through a respective channel or lumen formed in the tapered distal tip wherein the first and second guidewires guide the stent-graft into a position within a main vessel such that the first end of the tubular graft aligns with or is positioned immediately distal of a distal edge of at least one of an ostia of a second and third branch vessel.

6. The system of claim 5, wherein said at least one undulating spring element has an eyelet.

7. The system of claim 6, wherein said undulating spring element eyelet is overlapped with said eyelet in said graft material such that the first guidewire extends through each of the eyelets.

8. The system of claim 5, wherein said graft material has a second eyelet formed therein at said first end that is sized to receive only a guidewire therethrough and wherein a distal opening of said second guidewire tube aligns with the second eyelet such that the second guidewire extends from the distal opening of the second guidewire tube and through the second eyelet.

9. The system of claim 8, wherein said at least one undulating spring element has two eyelets each being overlapped with one of said graft material eyelets such that the respective first or second guidewires that extends through the graft material eyelet also extends through the respective overlapped eyelet of the undulating spring element.

10. The system of claim 5 wherein the tapered distal tip includes first and second channels formed in an exterior surface thereof with the first guidewire extending through the first channel and the second guidewire extending through the second channel.

11. The system of claim 10 wherein the tapered distal tip includes a central guidewire lumen through which the third guidewire extends.

12. The system of claim 10 wherein prior to deployment of the stent-graft the first and second guidewires are held within respective first and second channels of the tapered distal tip by the sheath.

13. The system of claim 5, wherein a diameter of the eyelet is substantially equal to an inner diameter of the first guidewire tube.

14. A prosthesis delivery system comprising:

a delivery apparatus comprising a sheath and a tapered distal tip;

a stent-graft being disposed in said sheath, said stent-graft including a tubular graft comprising graft material and a proximal annular spring element having a distal end attached to said graft material to extend from a proximal end of the tubular graft, wherein the proximal annular spring element includes first and second eyelets;

a first guidewire tube having a first guidewire disposed therethrough, the first guidewire tube being positioned inside said stent-graft to align with the first eyelet such that the first guidewire extends through the first eyelet;

a second guidewire tube having a second guidewire disposed therethrough, the second guidewire tube being positioned inside said stent-graft to align with the second eyelet such that the second guidewire extends through the second eyelet; and a third guidewire tube having a third guidewire disposed therethrough and being positioned inside said stent-graft, wherein each of said first, second and third guidewires extends through a respective channel or lumen formed in the tapered distal tip wherein the first and second guidewires guide the stent-graft into a position within a main vessel such that the first end of the tubular graft aligns with or is positioned immediately distal of a distal edge of at least one of an ostia of a second and third branch vessel.

15. The system of claim 14, wherein a diameter of the first and second eyelets is substantially equal to an inner diameter of the first and second guidewire tubes, respectively.

16. The system of claim 14, wherein said first and second eyelets do not overlap with said graft material of said tubular graft.

17. The system of claim 16, wherein the distance between one of said first and second eyelets and said proximal end of said tubular graft is different than the distance between the other of said first and second eyelets and said proximal end of said tubular graft.

18. The system of claim 14, wherein said graft material has two cut outs within the proximal end of the tubular graft and each of said first and second eyelets is laterally aligned with a respective one of said two cut outs.

* * * * *